(12) United States Patent
Thompson

(10) Patent No.: US 8,377,115 B2
(45) Date of Patent: Feb. 19, 2013

(54) IMPLANTABLE VALVE PROSTHESIS FOR TREATING VENOUS VALVE INSUFFICIENCY

(75) Inventor: Dustin Thompson, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 427 days.

(21) Appl. No.: 12/618,881

(22) Filed: Nov. 16, 2009

(65) Prior Publication Data

US 2011/0118828 A1    May 19, 2011

(51) Int. Cl.
  *A61F 2/06* (2006.01)
  *A61F 2/24* (2006.01)

(52) U.S. Cl. ...... 623/1.24; 623/1.26; 623/2.1; 623/2.12; 623/2.14; 623/2.17; 623/2.18; 623/2.24

(58) Field of Classification Search ........ 623/2.17–2.18, 623/2.2; 251/12, 212, 902
See application file for complete search history.

(56) References Cited

U.S. PATENT DOCUMENTS

| | | | |
|---|---|---|---|
| 3,378,019 A | 4/1968 | Denis | |
| 3,417,777 A * | 12/1968 | De Balsac et al. | 137/843 |
| 5,713,917 A | 2/1998 | Leonhardt et al. | |
| 5,824,041 A | 10/1998 | Lenker et al. | |
| 5,855,601 A | 1/1999 | Bessler et al. | |
| 6,503,272 B2 * | 1/2003 | Duerig et al. | 623/1.24 |
| 6,668,849 B2 * | 12/2003 | Onstenk et al. | 137/1 |
| 6,705,585 B1 | 3/2004 | Roy | |
| 6,817,374 B2 * | 11/2004 | Onstenk et al. | 137/1 |
| 7,264,632 B2 | 9/2007 | Wright et al. | |
| 2004/0111111 A1 | 6/2004 | Lin | |
| 2004/0225353 A1 | 11/2004 | McGuckin et al. | |
| 2006/0178552 A1 | 8/2006 | Gross | |
| 2010/0152839 A1 * | 6/2010 | Shandas et al. | 623/1.24 |

FOREIGN PATENT DOCUMENTS

WO    WO2006/106511 A2    10/2006

OTHER PUBLICATIONS

U.S. Appl. No. 12/391,372, filed Feb. 24, 2009, Thompson et al.
Int'l Search Report for Int'l App. No. PCT/US2010/055299.

* cited by examiner

*Primary Examiner* — David Isabella
*Assistant Examiner* — Jacqueline Woznicki

(57) ABSTRACT

A valve prosthesis for percutaneous placement within a vein is disclosed that includes a valve scaffold and a backflow barrier. The valve scaffold is of a shape memory or resilient material and the backflow barrier is a flap of flexible material attached to the valve scaffold. The valve prosthesis is operable to alternate between open and closed configurations in response to changes in retrograde blood flow pressure. In the open configuration, the valve scaffold has a frustoconical coil shape of consecutive windings with open spaces therebetween and the backflow barrier allows antegrade blood flow through the open spaces. In the closed configuration, the consecutive windings of the valve scaffold are collapsed such that the valve scaffold has a substantially flat profile and the backflow barrier covers the opens spaces of the flattened valve scaffold to prevent retrograde blood flow from leaking there through.

12 Claims, 4 Drawing Sheets

IMPLANTABLE VALVE PROSTHESIS FOR TREATING VENOUS VALVE INSUFFICIENCY

FIELD OF THE INVENTION

The invention relates to valve prostheses for percutaneous placement within a vein.

BACKGROUND OF THE INVENTION

Venous valves are found within native venous vessels and are used to assist in returning blood back to the heart in an antegrade direction from all parts of the body. The venous system of the leg for example includes the deep venous system and the superficial venous system, both of which are provided with venous valves which are intended to direct blood toward the heart and prevent backflow or retrograde flow which can lead to blood pooling or stasis in the leg. Incompetent valves can also lead to reflux of blood from the deep venous system to the superficial venous system and the formation of varicose veins. Superficial veins which include the greater and lesser saphenous veins have perforating branches in the femoral and popliteal regions of the leg that direct blood flow toward the deep venous system and generally have a venous valve located near the junction with the deep system. Deep veins of the leg include the anterior and posterior tibial veins, popliteal veins, and femoral veins. Deep veins are surrounded in part by musculature tissues that assist in generating flow due to muscle contraction during normal walking or exercising. Veins in the lower leg of a healthy person may range from 0 mm Hg to over 200 mm Hg, depending on factors such as the activity of the body, i.e., stationary or exercising, the position of the body, i.e., supine or standing, and the location of the vein, i.e., ankle or thigh. For example, venous pressure may be approximately 80-90 mm Hg while standing and may be reduced to 60-70 mm Hg during exercise. Despite exposure to such pressures, the valves of the leg are very flexible and can close with a pressure drop of less than one mm Hg.

FIGS. 1A-1B are schematic representations of blood flow through a healthy native valve 104 within a vein 100. Valves within the venous system are configured in a variety of shapes that depend on anatomical location, vessel size, and function. For example, the shape of the venous valve may include leaflets or leaflets with sinuses. The natural venous valve leaflet configuration referenced herein is for clarity of function and is not limiting in the application of the referenced embodiments. Venous valve 104 controls blood flow through lumen 102 of vein 100 via leaflets 106, 108. More particularly, venous valve 104 opens to allow antegrade flow 112 through leaflets 106, 108 as shown in FIG. 1A. Venous valve 104 closes to prevent backflow or retrograde flow 114 through leaflets 106, 108 as shown in FIG. 1B.

Veins typically located in the leg can become distended from prolonged exposure to excessive pressure and due to weaknesses found in the vessel wall causing the natural venous valves to become incompetent leading to retrograde blood flow in the veins. Such veins no longer function to help pump or direct the blood back to the heart during normal walking or use of the leg muscles. As a result, blood tends to pool in the lower leg and can lead to leg swelling and the formation of deep venous thrombosis and phlebitis. The formation of thrombus in the veins can further impair venous valvular function by causing valvular adherence to the venous wall with possible irreversible loss of venous function. Continued exposure of the venous system to blood pooling and swelling of the surrounding tissue can lead to post phlebitic syndrome with a propensity for open sores, infection, and may lead to limb amputation.

Chronic Venous Insufficiency (CVI) occurs in patients that have deep and superficial venous valves of their lower extremities (distal to their pelvis) that have failed or become incompetent due to congenital valvular abnormalities and/or pathophysiologic disease of the vasculature. As a result, such patients suffer from varicose veins, swelling and pain of the lower extremities, edema, hyper pigmentation, lipodermatosclerosis, and deep vein thrombosis (DVT). Such patients are at increased risk for development of soft tissue necrosis, ulcerations, pulmonary embolism, stroke, heart attack, and amputations.

FIG. 2 is a schematic representation of blood flow through an incompetent venous valve. Valve leaflets 106, 108 do not completely close and thus allow some venous blood to flow in a retrograde direction. The retrograde flow or backflow 114 leaks through venous valve 104 creating blood build-up that eventually may destroy the venous valve and cause a distended area or venous wall bulge 110. More specifically, the vessel wall of vein 100 expands into a pouch or bulge, such that the vessel has a knotted appearance when the pouch is filled with blood. As the bulging progresses, vein 100 becomes further enlarged and valve leaflets 106, 108 move farther apart, allowing even more blood to backflow. Thus, once valve 104 becomes incompetent, the venous insufficiency/incompetency progressively worsens. The distended vessel wall area may occur on the outflow side of the valve above leaflets 106, 108 as shown in FIG. 2, and/or on the inflow side of the valve below leaflets 106, 108. After a vein segment becomes incompetent, the vessel wall dilates and fluid velocity there through decreases, which may lead to flow stasis and thrombus formation in the proximity of the venous valve.

Repair and replacement of venous valves presents a formidable challenge due to the low blood flow rate found in native veins, the very thin wall structure of the venous wall and the venous valve, and the ease and frequency of which venous blood flow can be impeded or totally blocked for a period of time. Surgical reconstruction techniques used to address venous valve incompetence include venous valve bypass using a segment of vein with a competent valve, venous transposition to bypass venous blood flow through a neighboring competent valve, and valvuloplasty to repair the valve cusps. These surgical approaches may involve placement of synthetic, allograft and/or xenograft prostheses inside of or around the vein. However, such prostheses have not been devoid of problems, such as thrombus formation and valve failure due to leaflet thickening/stiffening, non-physiologic flow conditions, non-biocompatible materials and/or excessive dilation of the vessels with a subsequent decrease in blood flow rates. In addition, many venous valve prostheses include leaflets and/or hinged flaps and are similar to valves placed into the heart, which are complex and designed for high blood pressures associated with the heart instead of lower venous blood pressures associated with veins in the lower extremities.

Percutaneous methods for treatment of venous insufficiency are being studied, some of which include placement of synthetic, allograft and/or xenograft prosthesis that suffer from similar problems as the surgically implanted ones discussed above.

In light of these limitations, there is a need for an improved device to restore normal venous circulation to patients suffering from venous valve insufficiency. The present disclosure is directed to a one-way valve prosthesis that may be percutaneously placed within a vein.

BRIEF SUMMARY OF THE INVENTION

Embodiments hereof are directed to an one-way venous valve prosthesis for percutaneous placement within a vein. The prosthesis has a body portion including a valve scaffold and a backflow barrier. The body portion is operable to alternate between an open configuration wherein the valve scaffold has a frustoconical coil shape of consecutive windings with open spaces therebetween, and a closed configuration wherein the consecutive windings of the valve scaffold are collapsed such that the valve scaffold has a flat profile. The backflow barrier allows blood flow through the open spaces between consecutive windings of the valve scaffold when the body portion is in the open configuration and the backflow barrier covers the open spaces between consecutive windings of the valve scaffold to prevent blood flow through the valve prosthesis when the body portion is in the closed configuration.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 4 is a perspective view of the valve prosthesis of FIG. 3, wherein the valve prosthesis is in a closed configuration to prevent blood flow there through.

DETAILED DESCRIPTION OF THE INVENTION

Figures 1A, 1B, 2:
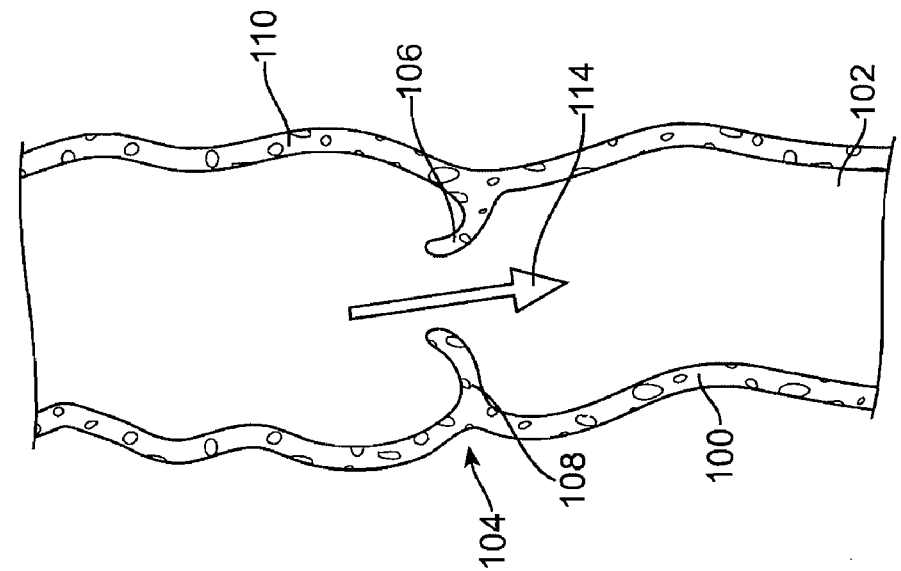
FIGS. 1A-1B are schematic representations of blood flow through a healthy valve within a vein.
FIG. 2 is a schematic representation of blood flow through an incompetent valve within a vein.

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

The following detailed description is merely exemplary in nature and is not intended to limit the invention or the application and uses of the invention. Although the description of the invention is in the context of treatment of blood vessels such as the superficial and deep veins of a leg, the invention may also be used in any other body passageways where it is deemed useful. Furthermore, there is no intention to be bound by any expressed or implied theory presented in the preceding technical field, background, brief summary or the following detailed description.

Referring to FIGS. 3, 3A, 4 and 4A, a venous valve prosthesis 316 for treating chronic venous insufficiency according to an embodiment hereof is shown. Valve prosthesis 316 has a body portion 318 that includes a valve scaffold 320 and a backflow barrier 322. Valve scaffold 320 of body portion 318 is attached to a self-expanding annular anchor or stent 325 for securing valve prosthesis 316 within a vessel, as will be described in more detail below with respect to FIG. 6. When implanted in vivo valve prosthesis 316 opens and closes in response to changes in antegrade and retrograde blood flow to mimic venous valve operation. Body portion 318 of valve prosthesis 316 is operable to alternate between a preset open configuration shown in FIG. 3, in which backflow barrier 322 allows blood flow through valve prosthesis 316, and a closed configuration shown in FIG. 4, in which backflow barrier 322 prevents blood flow through valve prosthesis 316.

Figure 3:
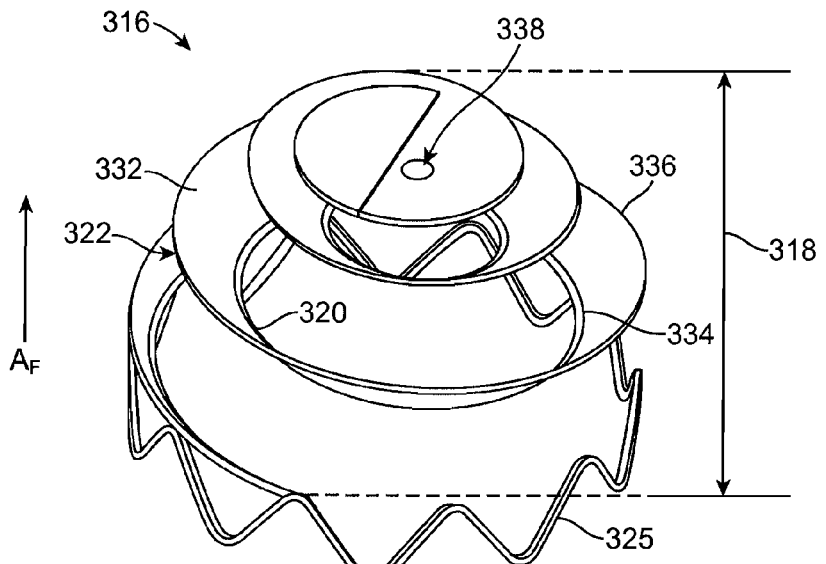
FIG. 3 is a perspective view of a valve prosthesis according to an embodiment hereof, wherein the valve prosthesis is in a preset open configuration.
Figure 3A:
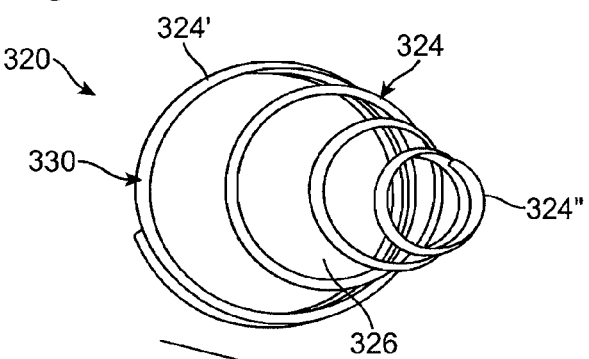
FIG. 3A is a side perspective view of a valve scaffold of the valve prosthesis of FIG. 3 shown in the preset open configuration.

FIG. 3A illustrates valve scaffold 320 separated from valve prosthesis 316 as shown in FIG. 3. In the preset open configuration, valve scaffold 320 is a wire-like or tubular structure 330 having a frustoconical coil or spring shape formed by a series of consecutive loops or windings 324 with open spaces 326 therebetween. A single winding 324 of valve scaffold 320 may also be described mathematically as a helical torus wherein the generally toroidal or "doughnut" shape is formed out of plane by one turn of a helix. The outer diameters of windings 324 gradually decrease from a base winding 324' to a nose winding 324". When valve prosthesis 316 is placed within a vein in vivo nose winding 324" of valve scaffold 320 is situated upstream of base winding 324' of valve scaffold 320 such that antegrade blood flow is in a direction indicated by arrow 328. Although four windings 324 are shown in the embodiment of FIG. 3A, more or fewer windings may be used without departing from the scope of the present invention.

In various embodiments in accordance herewith, wire-like structure 330 may be solid or hollow and have a circular cross-section with a diameter between 0.002 inches and 0.015 inches. In another embodiment, the cross-section of wire-like structure 330 may be an oval, square, rectangular, or any other suitable shape. Wire-like structure 330 of valve scaffold 320 is formed from a biocompatible shape memory material or a biocompatible resilient material that permits valve scaffold 320 to be deformed during delivery and/or during valve operation and thereafter returns valve scaffold 320 to the preset longitudinally extended shape depicted in FIG. 3A, which may also be referred to as a frustoconical coil shape. A "shape memory" material as used herein refers to a material that exhibits shape memory, which is the ability of the material to be severely deformed and then returned to its original shape simply by a change in temperature, and/or super (or hyper)-elasticity, which is an almost rubber-like flexibility demonstrated by the material to spring back to its original shape after loading that does not require a change in temperature. A heat or thermal treatment may be used to set the shape of wire-like structure 330 of a shape memory alloy, such as nitinol. For example, wire-like structure 330 of nitinol may be preset or shape-set into the frustoconical coil shape shown in FIG. 3A using an oven set to, by e.g., 525° C. In another embodiment, a shape memory to return to the frustoconical coil shape may be imparted to a polymer that forms wire-like structure 330, such as any of the polymers disclosed in U.S. Pat. Appl. Pub. No. 2004/0111111 to Lin, which is incorporated by reference herein in its entirety. "Resilient" and "resilience" as used herein to refer to a material for forming wire-like structure 330 means the structure formed of the material is capable of recovering an original set shape or form after being elastically stretched, deformed, compressed, or the like. In an embodiment, wire-like structure 330 of valve scaffold 320 may be made from a metallic material having a high resilience to return to the frustoconical coil shape after bearing a load. In addition, a mechanical memory to return to its original shape after being loaded may be imparted to wire-like structure 330 by thermal treatment to achieve a spring temper in stainless steel or cobalt chromium alloys, for example Conichrome®, Phynox® and Elgiloy®.

Backflow barrier 322 is a continuous flap 332 of a non-thrombogenic flexible material attached to wire-like structure 330 of valve scaffold 320. Prior to attachment to wire-like structure 330, flap 332 may have a rectangular shape. In another embodiment, flap 332 may have the form of a spiral-cut circle prior to attachment to wire-like structure 330. As used herein, a flap is a moveable piece of flexible material that has at least a portion of an edge thereof attached to wire-like structure 330. Accordingly, a first inner edge 334 of flap 332 is attached to wire-like structure 330 while a second outer edge 336 of the flap 332 is unattached to valve scaffold 320 such that flap 332 is movable by blood flow as discussed further below. Inner edge 334 of flap 332 may be attached to wire-like structure 330 by any suitable means known to those skilled in the art, for example and not by way of limitation, welding, adhesive, overmolding, suture, or mechanical coupling. In one embodiment, wire-like structure 330 may extend within a hem or fold of flap 332 extending along inner edge 334. Backflow barrier 322 extends from nose winding 324" to base winding 324' of wire-like structure 330 to be attached by first inner edge 334 for the entire coiled length of valve scaffold 320. In an alternate embodiment, the backflow barrier may cover less than the entire coiled length of the valve scaffold. Flap 332 has a thickness between 0.0005 inches and 0.0050 inches. Flap 332 may be formed from a biocompatible, non-thrombogenic material such as but not limited to expanded polytetrafluoroethylene (ePTFE), polytetrafluoroethylene (PTFE), Dacron, silicone, and polyesters. Such thin and lightweight materials minimize the amount of pressure or blood flow required to open and close the valve prosthesis, thus more closely mimicking native valve operation and avoiding stasis or blood pooling at the deployment site of the valve prosthesis, which may lead to the formation of thrombosis thereon.

As illustrated in FIG. 3, when body portion 318 of valve prosthesis 316 is in the preset open configuration, antegrade blood flow represented by arrow $A_F$ pushes outer edge 336 of backflow barrier 322 away from valve scaffold 320 so that backflow barrier 322 does not cover open spaces 326 of valve scaffold 320 and thus allows blood flow through open spaces 326 between consecutive windings 324 of valve scaffold 320. Thus, in situ, flap 332 of backflow barrier 322 is displaced in the direction of antegrade blood flow.

Figure 4:
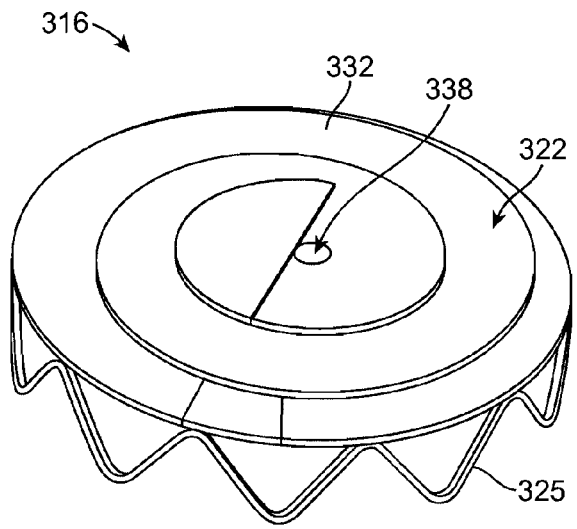
Figure 4A:
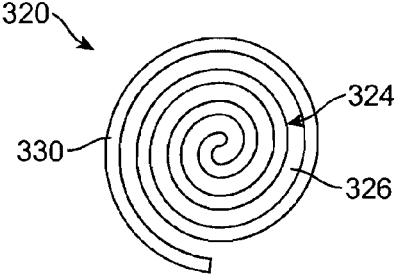
FIG. 4A is a top view of the valve scaffold of the valve prosthesis of FIG. 4.

In FIG. 4 valve prosthesis 316 is shown in a closed configuration and FIG. 4A illustrates valve scaffold 320 separated from valve prosthesis 316 as shown in FIG. 4. When body portion 318 of valve prosthesis 316 is in the closed configuration, consecutive windings 324 of valve scaffold 320 are collapsed into a substantially flat or pancake-like profile having an approximate thickness or diameter of wire-like structure 330, and flap 332 of backflow barrier 322 covers open spaces 326 of valve scaffold 320 in order to prevent retrograde blood flow from leaking through valve prosthesis 316. When backflow pressure closes valve prosthesis 316, as discussed in more detail below, flap 332 is prevented from being displaced in the direction of the retrograde blood flow due to interference with downstream portions of valve scaffold 320 and/or with downstream portions of itself. Once outer edge 336 of flap 332 is pushed against wire-like structure 330 of valve scaffold 320 and/or against downstream portions of itself, flap 332 operates as a barrier to backflow. Outer edge 336 of flap 332 may overlap inner edge 334 of flap 332 when valve prosthesis 316 is in the closed configuration to ensure that valve prosthesis 316 does not collapse or cave-in under backflow pressure. The width of flap 332 is thus dependent upon the number of windings 324 and the diameter of the target body vessel. In one embodiment, outer edge 336 of flap 332 overlaps inner edge 334 of flap 332 between one and four times the thickness of wire-like structure 330. As shown in FIG. 4, center 338 of valve prosthesis 316 may have a small opening when in the closed configuration. Such a small opening may allow some backflow leakage through valve prosthesis 316 that will not affect the function of the valve prosthesis in substantially reducing reflux and preventing long-term retrograde backflow. Alternatively, center 338 of valve prosthesis may be covered such that there is no opening in valve prosthesis 316 when in the closed configuration. In such an embodiment, a portion of flap 332 may be sized to cover center 338, or a flared tip (not shown) may be attached to an end of nose winding 324" of wire-like structure 330 to essentially plug center 338 of the valve prosthesis when in the closed configuration.

Figure 5:
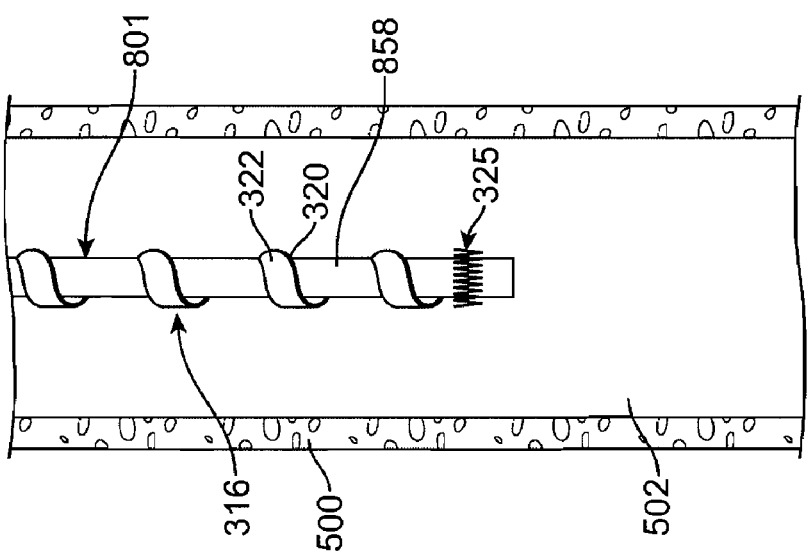
FIG. 5 is a schematic sectional view of the valve prosthesis shown in FIG. 3 being delivered to a treatment site within a vein, wherein the prosthesis is in a delivery configuration.

The operation of valve prosthesis 316 transitioning between the preset open configuration of FIG. 3, in which valve scaffold 320 is in its frustoconical coil shape, and the closed configuration of FIG. 4, in which valve scaffold 320 assumes a flat profile, for regulating blood flow through the valve prosthesis is described with reference to FIGS. 5-7. FIG. 5 is a schematic sectional view of valve prosthesis 316 being transluminally positioned or delivered to a treatment site within a vein 500 having an incompetent native valve (not shown). As shown in the delivery configuration, valve scaffold 320 and attached backflow barrier 322 resemble a ribbon would around a distal end of a delivery system, such as delivery system 801 described further below. The resilient or shape memory material of wire-like structure 330 permits valve scaffold 320 to be substantially stretched and therefore compressed into a low profile for delivery to the treatment site. The delivery configuration depicted in FIG. 5 allows valve prosthesis 316 to be mounted onto a low profile delivery system that can access small vessels such as superficial veins. Valve prosthesis 316 is delivered to and deployed within vein 500 in a percutaneous manner, as described in further detail below, and is positioned at a target location within lumen 502 of vein 500 where valve prosthesis 316 is to be implanted. It should be understood by one of skill in the art that methods as described herein may be used in any vein suffering from chronic venous insufficiency, including but not limited to superficial veins and deep veins.

When valve prosthesis 316 is deployed within vein 500, wire-like structure 330 returns to or assumes its preset frustoconical coil shape in which it coils, winds or spirals into a series of windings 324. FIG. 6 is a schematic view of valve prosthesis 316 in its open configuration deployed within vein 500 showing valve scaffold 320 returned to its frustoconical coil shape. As shown in FIG. 6, valve prosthesis 316 need not be placed adjacent to the incompetent valve but rather may be implanted at any location along vein 500 to operate effectively. However, in an embodiment, the target location may be adjacent to the valve leaflets of the incompetent valve. If implanted adjacent to the incompetent valve, the valve prosthesis may arrest, by means of anchor or stent 325, the progressive damage to vein 500 caused by the marginal function of the native valve by protecting the damaged venous wall from further blood pooling, thereby allowing the native valve to scar and/or heal.

Figure 6:
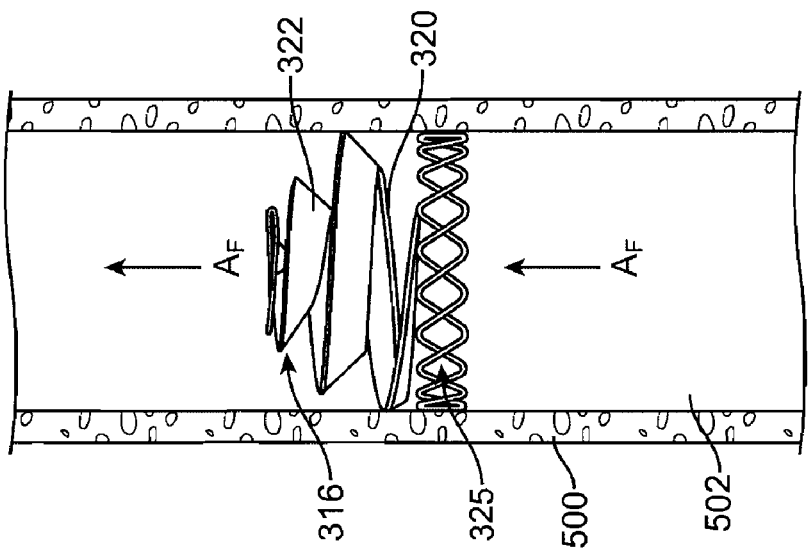
FIG. 6 is a schematic sectional view of the valve prosthesis shown in FIG. 3 placed within a vein, wherein the prosthesis is in the open configuration.

As also shown in FIG. 6, valve prosthesis 316 is secured to the wall of vein 500 by anchor or stent 325. Anchor 325 is an annular, self-expanding structure having a sinusoidal pattern that is attached to valve scaffold 320 in order to prevent migration of the valve prosthesis. A self-expanding anchor 325 may be deployed upon release from a restraining mechanism such as a retractable sheath to bias valve prosthesis 316 into conforming fixed engagement with an interior surface of vein 500. In an embodiment, an anchor may be constructed of a shape memory material such as nickel-titanium (nitinol) and have any suitable configuration known to one of skill in the art. Examples of suitable annular support members that may be used as anchor 325 are described, for example, in U.S. Pat. No. 5,713,917 to Leonhardt et al. and U.S. Pat. No. 5,824,041 to Lenker et al., which are incorporated by reference herein in their entirety. When used with valve prosthesis 316, anchor 325 has sufficient radial spring force and flexibility to conformingly engage the prosthesis with the body lumen inner wall. In an embodiment, a series of barbs or protrusions (not shown) may be attached to protrude from an outer surface of anchor 325 that lodge or embed within the vein walls to securely fix valve prosthesis 316 within vein 500. The barbs may be pointed or spiked or have other configurations suitable for lodging within the vein walls.

Once deployed and implanted in vein 500, valve prosthesis 316 mimics native venous valve operation by allowing blood to flow there through in only an antegrade direction to thereby control backflow through lumen 502 of vein 500. As described above with respect to FIG. 3, when valve prosthesis 316 is in the open configuration, antegrade blood flow $A_F$ displaces backflow barrier 322 so that blood may flow through valve prosthesis 316, and more particularly through open spaces 326 between consecutive windings 324 of valve scaffold 320. Generally, valve prosthesis 316 in the open configuration permits a flow of blood through vein 500 at a rate of about 0.25 L/min to about 5 L/min.

Figure 7:
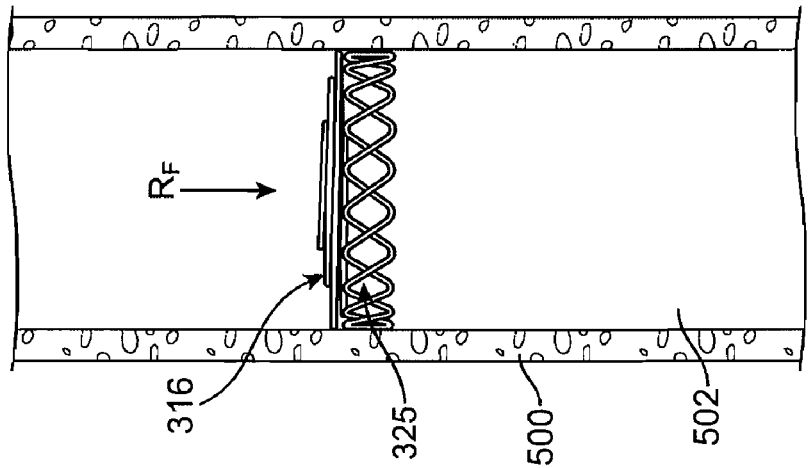
FIG. 7 is a schematic sectional view of the valve prosthesis shown in FIG. 3 placed within a vein, wherein the prosthesis is in the closed configuration.

As shown in FIG. 7, valve prosthesis 316 closes in response to sufficient retrograde blood flow pressure to have a substantially flat profile. When blood flow through the vein changes direction, i.e., retrograde blood flow $R_F$ or backflow occurs due to changing pressure differentials across the new valve, the retrograde blood flow pressure causes the frustoconical coil shape of valve scaffold 320 to flatten or collapse and transforms valve prosthesis 316 into the closed configuration. More particularly as retrograde blood flow $R_F$ acts against flap 332 of valve prosthesis 316, the force is transferred to valve scaffold 320 and the frustoconical coil shape of valve scaffold 320 is flattened such that outer edge 336 of continuous flap 332 of backflow barrier 322 overlaps with inner edge 334 of downstream winding 324 of valve scaffold 320 whereby flap 332 covers open spaces 326 between the windings 324. In this manner, backflow barrier 322 prevents or substantially reduces gravitational or retrograde blood flow $R_F$ from backflowing through valve prosthesis 316. Valve prosthesis 316 preferably can withstand retrograde blood flow pressures greater than 150 mmHg with less than 1.0 mL/min of leakage. Valve prosthesis 316 may be designed to withstand such retrograde blood flow pressures by manipulating several factors, including the diameter or thickness of wire-like member 330 of valve scaffold 320, the thickness of backflow barrier 322, and the number of consecutive windings 324 of valve scaffold 320. In general, increased values of these factors will result in valve prosthesis 316 being able to withstand higher retrograde blood flow pressures. Advantageously, valve prosthesis 316 in the flattened closed configuration does not include pockets or sinuses that are prone to pooling backflow blood that may result in clots.

More particularly, valve prosthesis 316 is designed to collapse into the closed configuration when the retrograde blood flow $R_F$ exerts a head pressure of a given load or threshold value that is sufficient to deform valve scaffold 320 into a flattened profile. In the preset open configuration valve prosthesis 316 has a resistance to closing that may depend on several factors in addition to the shape memory or resilient material from which it is formed, including material stiffness of valve scaffold 320, material thickness of valve scaffold 320, and/or the geometry of valve scaffold 320. By manipulating these factors, valve prosthesis 316 may be designed to collapse or flatten into the closed configuration under predetermined pressure threshold values that depend on the particular implantation site of the valve prosthesis within the vasculature. Accordingly, the design and dimensions of valve scaffold 320 may be selected such that valve prosthesis 316 collapses or flattens at a certain, predetermined pressure threshold value. For example, the diameter or thickness of wire-like member 330 of valve scaffold 320 may be chosen such that valve prosthesis 316 will close at the predetermined pressure threshold value. In general, greater diameters or thicknesses of wire-like member 330 will result in valve prosthesis 316 having a greater resistance to closing. In addition, the pitch or spacing between windings 324 will affect the valve prosthesis's resistance to closing. In general, smaller spaces between windings 324 will result in valve prosthesis 316 having a greater resistance to closing. In addition, the material of wire-like member 330 of valve scaffold 320 may be chosen such that valve prosthesis 316 will close at the predetermined pressure threshold value. The stiffness of the material of valve scaffold 320 also affects the valve prosthesis's resistance to closing, with stiffer materials having a greater resistance to closing. Stiffness refers to the resistance of wire-like structure 330 to deflection or deformation by an applied force. Further, the transition temperature of the material of valve scaffold 320 will affect the valve prosthesis's resistance to closing. For example, when valve scaffold is formed from nitinol, the transition temperature may be set at body temperature such that valve prosthesis 316 has a higher stiffness and therefore a greater resistance to closing upon implantation. Alternatively, the transition temperature may be set higher than body temperature such that valve prosthesis 316 has a lower stiffness and therefore less resistance to closing when implanted. In one embodiment, the predetermined pressure threshold value at which valve prosthesis will begin to close is approximately 50 mmHg. As such, valve prosthesis 316 is normally open to blood flow and will close only when retrograde blood flow pressure exceeds the predetermined pressure threshold value, such as when the patient stands up. When there is insufficient retrograde blood flow pressure to maintain valve scaffold 320 in its flattened profile, the shape memory or resiliency of the material that forms wire-like structure 330 causes valve prosthesis 316 to recover or be restored to the preset open configuration.

Embodiments of the valve prostheses described herein are preferably delivered in a percutaneous, minimally invasive manner and may be delivered by any suitable delivery system. In contrast to surgically placed valves that require incisions and suturing at the sight of the native valve, percutaneous delivery of a replacement valve can mitigate thromboses formed from an injury response. In general, a venous valve prosthesis in accordance with embodiments hereof having at least one self-expanding anchor is loaded into a sheathed delivery system, compressing the self-expanding anchor(s). As previously described, the self-expanding anchors may have a sinusoidal patterned configuration or may have an annular band configuration. Initially luminal access to a desired peripheral vein, such as the greater or lesser saphenous, femoral, or popliteal veins, is obtained using standard percutaneous techniques such as the Seldinger technique as would be understood by one of ordinary skill in the art. Access to the venous vasculature may be achieved through a branch of the femoral vein, or alternatively, may be achieved through a branch of the subclavian vein. A guidewire is maneuvered to a treatment site within the vein where the valve prosthesis is to be implanted. The treatment site may be located upstream or downstream of leaflets of an insufficient native valve. The delivery system is then threaded or tracked through the vascular system of the patient over the guidewire until the valve prosthesis is located within a predetermined target site. Once properly positioned, the sheath of the delivery system is removed to allow the anchors to self-expand, appose the venous wall, and secure the valve prosthesis within the vein. Once the venous valve prosthesis is properly positioned at the target site, the delivery system may be retracted and removed from the patient.

Figure 8:
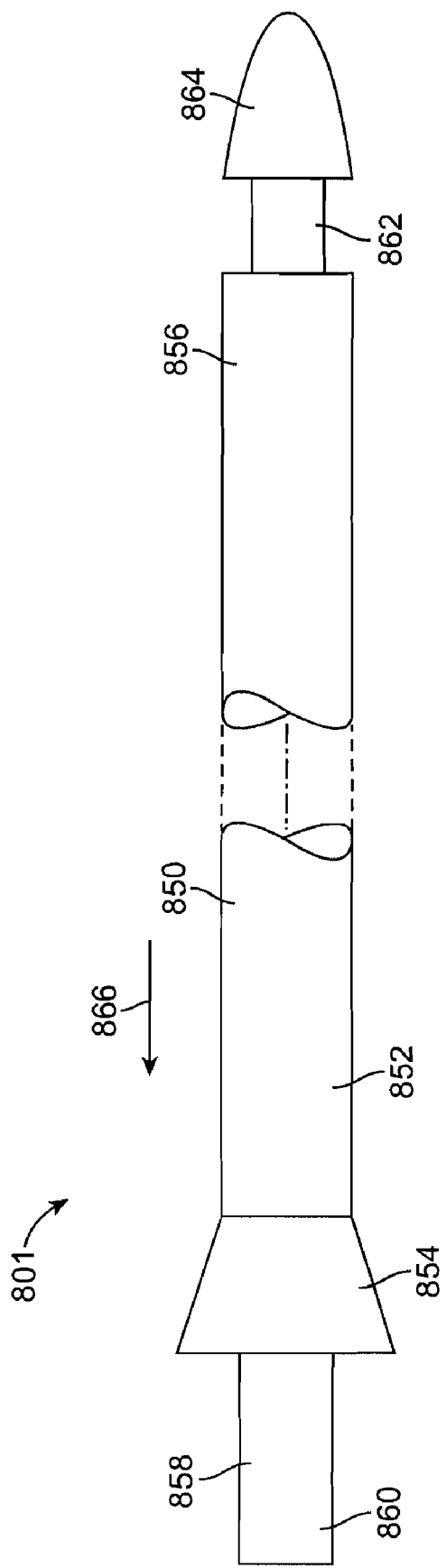
FIG. 8 is an example of a delivery system for delivering the valve prosthesis shown in FIG. 3.

For example, FIG. 8 illustrates a schematic side view of an exemplary delivery system 801 for delivering and deploying valve prosthesis 316 as described above. Delivery system 801 includes a retractable outer shaft 850 having a proximal end 852 and a distal end 856, and an inner shaft 858 having a proximal end 860 and a distal end 862. Outer shaft 850 defines a lumen extending there through (not shown), and inner shaft 858 slidably extends through the lumen of outer shaft 850 to a distal tip 864 of the delivery system. Distal tip 864 is coupled to distal end 862 of inner shaft 858, and may be tapered and flexible to provide trackability in tight and tortuous vessels. In an embodiment, inner shaft 858 may define a guidewire lumen (not shown) for receiving a guidewire there through or may instead be a solid rod without a lumen extending there through.

Valve prosthesis 316 is mounted on distal end 862 of inner shaft 858 as shown in FIG. 5. Valve prosthesis 316 has a compressed diameter and an increased length when mounted on the distal end of the delivery system, and valve scaffold 320 and attached backflow barrier 322 resemble a ribbon wound around inner shaft 858. Valve prosthesis 316 may be mounted on distal end 862 of inner shaft 858 by any suitable manner known in the art, such as self-expanding attachment bands, a cap coupled to the distal end of inner shaft 858 to retain the valve prosthesis in a radially compressed configuration, and/or the inclusion of slots, ridges, pockets, or other prosthesis retaining features (not shown) formed into the exterior surface of inner shaft 858 to secure the valve prosthesis in frictional engagement with delivery system 801. Outer shaft 850 covers and constrains valve prosthesis 316 while delivery system 801 is tracked through a body lumen to the deployment site. Outer shaft 850 is movable in an axial direction along and relative to inner shaft 858 and extends to a proximal portion of delivery system 801 where it may be controlled via an actuator, such as a handle 854, to selectively release valve prosthesis 316. When the actuator is operated, outer shaft 850 is retracted over inner shaft 858 in a proximal direction as indicated by directional arrow 866 such that valve prosthesis 316 is released and allowed to assume its preset open configuration. An exemplary suitable delivery system is described in U.S. Pat. No. 7,264,632 to Wright et al., which is hereby incorporated by reference in its entirety.

Although the valve prosthesis is described herein as self-expanding for percutaneous placement, it should be understood that the valve prosthesis may alternatively be surgically implanted within a vein in a non-percutaneous manner and may be anchored to the vein in any suitable manner, such as via sutures, clips, or other attachment mechanisms. For example, in such a surgical embodiment, the valve scaffold may include a series of drilled holes through which sutures can be passed.

In another embodiment hereof, a valve prosthesis may be designed for use in the heart such as in the aorta location as well as other extravascular applications. In contrast to venous valve prosthesis 316, the heart valve prosthesis may be preset or heat-set in the closed configuration and be designed to open or expand to the open configuration in response to antegrade flow after it exceeds a blood flow pressure of a threshold value.

Embodiments of the valve prostheses described herein may include an anti-coagulant coating on one or more blood-contacting surfaces of the valve scaffold and/or the backflow barrier in order to mitigate hypercoagulability, which can be associated with foreign materials in the bloodstream. In one embodiment, an anti-coagulant material may be embedded in the material of the valve scaffold and/or the backflow barrier. The anti-coagulant material may be heparin, coumadin, aspirin, ticlopidine, clopidogrel, prasugrel or other suitable anti-coagulant pharmaceuticals. One suitable commercially available product by Carmeda of Sweden offers a clinically proven hemocompatible surface coating designed to actively reduce thrombus formation or clotting on blood-contacting medical devices. Carmeda's BioActive Surface technology mimics the natural vessel wall to create a blood-compatible surface and also allows for a robust heparin coating to ensure long-term biocompatibility.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:
1. A valve prosthesis comprising:
a valve scaffold having a coil shape of consecutive windings with open spaces therebetween, wherein the valve scaffold is formed from a first material selected from one of a shape memory material and a resilient material; and
a backflow barrier that is a flap of a second material attached along a first edge to the valve scaffold and having an opposing second edge free of the valve scaf- fold, the second material being different from the first material, wherein the valve prosthesis is operable to alternate between an open configuration wherein the consecutive windings of the valve scaffold form a frustoconical coil shape and the backflow barrier allows blood flow through the open spaces between consecutive windings of the valve scaffold, and a closed configuration wherein the consecutive windings of the valve scaffold are collapsed such that the valve prosthesis has a substantially flat profile and the backflow barrier covers the open spaces of the collapsed valve scaffold to prevent blood flow through the valve prosthesis.

2. The valve prosthesis of claim 1, wherein the valve scaffold is formed from a wire-like structure that is preset in the frustoconical coil shape.

3. The valve prosthesis of claim 1, wherein an upstream free second edge of the flap overlaps with a downstream attached first edge of the flap when the valve prosthesis is in the closed configuration.

4. The valve prosthesis of claim 1, wherein the valve prosthesis collapses to the closed configuration in response to retrograde blood flow pressure of a predetermined pressure threshold value that is sufficient to compress the valve scaffold into the substantially flat profile and the valve prosthesis returns to the open configuration when the retrograde blood flow pressure is insufficient to maintain the valve scaffold in the substantially flat profile such that the valve scaffold returns to the frustoconical coil shape.

5. The valve prosthesis of claim 4, wherein the predetermined pressure threshold value is approximately 50 mmHg.

6. The valve prosthesis of claim 1, further comprising:
an annular self-expanding anchor attached to the valve scaffold, wherein the anchor is operable to expand in radial apposition to a wall of a vessel.

7. The valve prosthesis of claim 6, further comprising:
barbs attached to an outer surface of the anchor, wherein the barbs are operable to lodge within the vessel wall of the vein.

8. The valve prosthesis of claim 1, wherein the backflow barrier is a continuous flap and the second material is selected from the group consisting of expanded polytetrafluoroethylene (ePTFE), polytetrafluoroethylene (PTFE), Dacron, silicone, and polyester, and wherein the backflow barrier has a thickness sufficient to allow the flap to be moveable by blood flow.

9. The valve prosthesis of claim 1, wherein the valve scaffold has a thickness between 0.002 inches and 0.015 inches.

10. The valve prosthesis of claim 1, wherein the valve prosthesis in the closed configuration is operable to remain closed in response to retrograde blood flow pressures of at least 150 mmHg.

11. The valve prosthesis of claim 1, wherein the valve scaffold extends within a hem of the backflow barrier.

12. The valve prosthesis of claim 1, wherein the valve prosthesis includes a series of consecutive windings that extend from a nose winding to a base winding and the backflow barrier extends from the nose winding to the base winding for the entire coiled length of the valve scaffold.

* * * * *

UNITED STATES PATENT AND TRADEMARK OFFICE
CERTIFICATE OF CORRECTION

| | | |
|---|---|---|
| PATENT NO. | : 8,377,115 B2 | Page 1 of 1 |
| APPLICATION NO. | : 12/618881 | |
| DATED | : February 19, 2013 | |
| INVENTOR(S) | : Thompson et al. | |

It is certified that error appears in the above-identified patent and that said Letters Patent is hereby corrected as shown below:

On the Title Page

Item (57) Abstract, line 14

"backflow barrier covers the opens spaces of the flattened"

should be changed to

--backflow barrier covers the open spaces of the flattened--

Signed and Sealed this
Eighteenth Day of June, 2013

Teresa Stanek Rea
*Acting Director of the United States Patent and Trademark Office*